US011077741B2

(12) United States Patent
Kosar et al.

(10) Patent No.: US 11,077,741 B2
(45) Date of Patent: Aug. 3, 2021

(54) VEHICLE CUP AIR PURIFYING DEVICE

(71) Applicant: Aeron Lifestyle Technology, Inc., Fairfield, IA (US)

(72) Inventors: Patrick J. Kosar, Fairfield, IA (US); Jerome L. Clock, Hampton, IA (US); Christopher E. Young, Rushville, IL (US); Patrick Guerin, Fairfield, IA (US)

(73) Assignee: Aeron Lifestyle Technology, Inc., Fairfield, IA (US)

( * ) Notice: Subject to any disclaimer, the term of this patent is extended or adjusted under 35 U.S.C. 154(b) by 240 days.

(21) Appl. No.: 16/411,603

(22) Filed: May 14, 2019

(65) Prior Publication Data
US 2020/0361290 A1     Nov. 19, 2020

(51) Int. Cl.
| *B60H 3/06* | (2006.01) |
| *B01D 35/30* | (2006.01) |
| *B01D 46/00* | (2006.01) |
| *B60H 3/00* | (2006.01) |
| *B01D 46/24* | (2006.01) |

(52) U.S. Cl.
CPC ........... *B60H 3/0658* (2013.01); *B01D 35/30* (2013.01); *B01D 46/0005* (2013.01); *B01D 46/24* (2013.01); *B60H 3/0014* (2013.01)

(58) Field of Classification Search
CPC .... B01D 35/30; B01D 46/24; B01D 46/2411; B01D 46/0005; B60H 3/0658
See application file for complete search history.

(56) References Cited

U.S. PATENT DOCUMENTS 10,859,290 B2 *   12/2020   Herweck ................... F24F 6/00

FOREIGN PATENT DOCUMENTS

| CN | 204319972 U | * 5/2015 | ............. B01D 46/10 |
| CN | 204730341 U |   10/2015 | |

OTHER PUBLICATIONS

CN204730341—English translation.

* cited by examiner

*Primary Examiner* — Robert A Hopkins
(74) *Attorney, Agent, or Firm* — Zarley Law Firm, P.L.C.

(57) ABSTRACT

A vehicle cup air purifying device includes a top housing connected to a base housing, both of which have a plurality of air vents. Disposed within the base housing is a filter. Also disposed within the base housing is an inner housing positioned above the filter and connected to the top housing to form a conduit.

20 Claims, 2 Drawing Sheets

VEHICLE CUP AIR PURIFYING DEVICE

BACKGROUND OF THE INVENTION

The present invention is directed to an air purifying device and more particularly an air purifying device adapted to be used with a vehicle cup holder.

Air purifying devices for vehicles are well known in the art. Typically, these purifiers are used in a conventional 12 volt socket. While useful, these devices do not blend in with the aesthetics of the vehicle, they don't provide multi-layer filtration, and they are not meant for purifying the personal space around the driver and/or passenger personal space. Therefore, a need exists in the art for a device that addresses the deficiencies.

As such, an objective of the present invention is to provide an air purifying device that compliments a vehicle space by sitting in and providing a vehicle cup holder.

Another objective is to provide an air purifying device having multi-layer filtration.

A still further objective is to provide an air purifying device that is directed to the personal space of the driver and/or passenger.

These and other objectives will be apparent to those having ordinary skill in the art based upon the following written description, drawings, and claims.

SUMMARY OF THE INVENTION

A vehicle cup air purifying device includes a top housing connected to a base housing. The base housing has a plurality of vertically disposed air vents that are preferably recessed. Disposed in the base housing is a filter and filter material.

An inner housing is positioned above the filter within the base housing and is connected with the top housing to form conduits for airflow. A blower connected to a main circuit board are disposed within the inner housing.

The top housing has a side wall and a bottom wall that form a chamber adapted to receive a beverage container. Extending outwardly and downwardly from a top edge of the top housing is a rim. The rim is connected to the inner housing and has recessed portions that form a portion of the conduits. Air vents are positioned on the rim to align with the conduits.

The housing contains a main circuit board, which is connected to a second circuit board, which in turn is connected to a glow ring, a button, and a USB connector.

DETAILED DESCRIPTION

Figure 2:
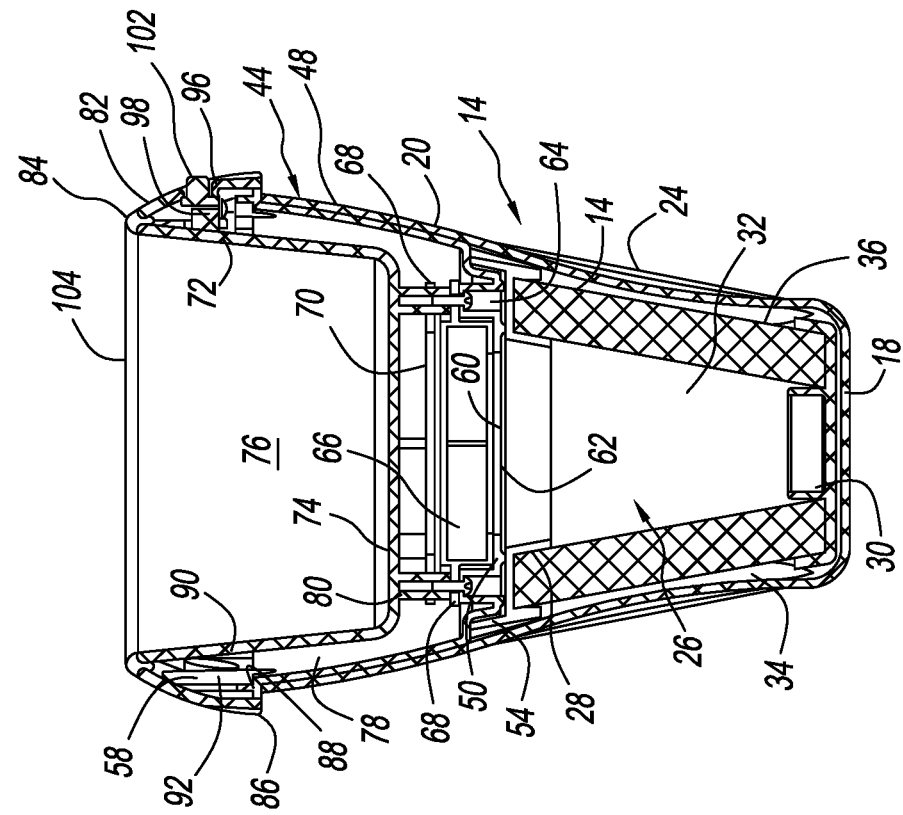
FIG. 2 is a side sectional view of an air purifying device.
Figure 1:
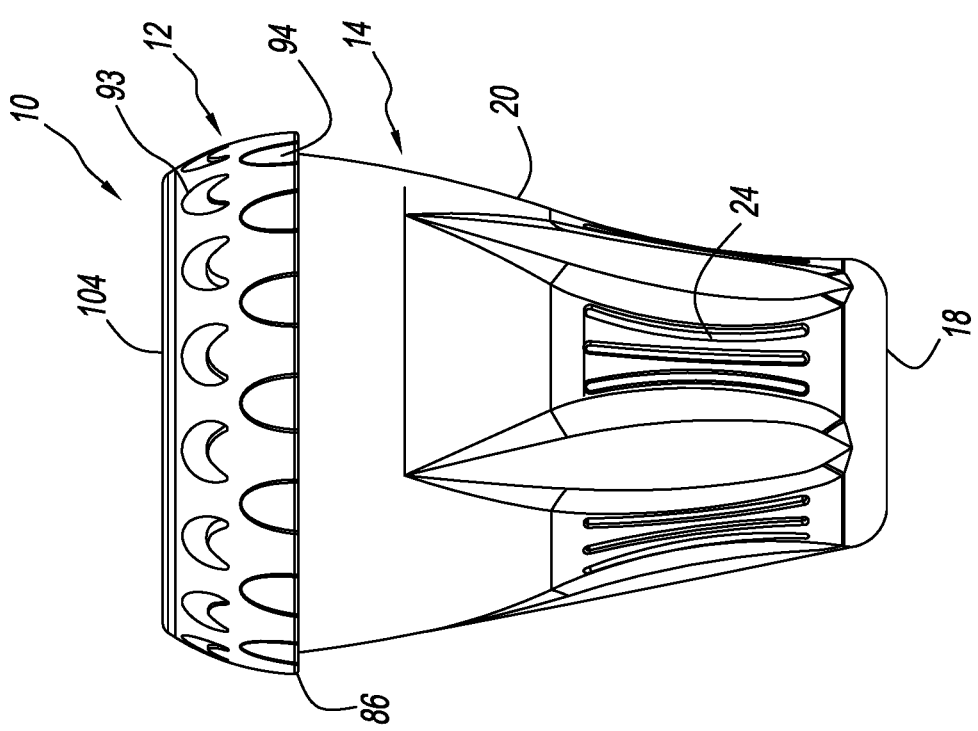
FIG. 1 is a side view of an air purifying device.
Figure 3:
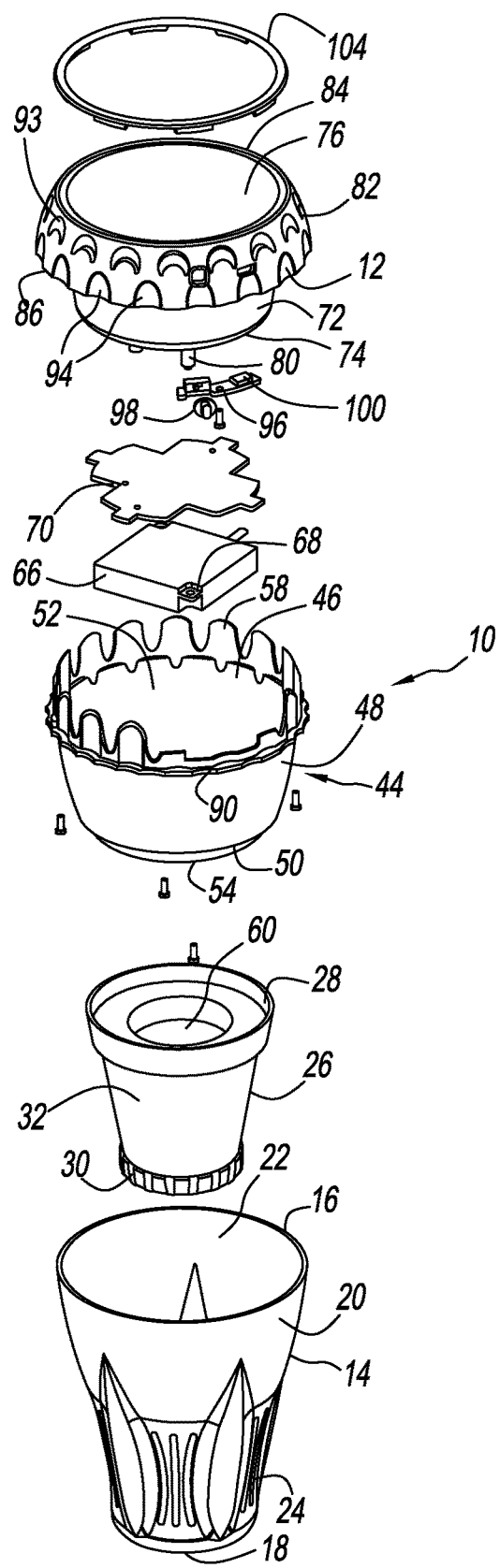
FIG. 3 is an exploded perspective view of an air purifying device.

A vehicle cup air purifier 10 includes an outer or top housing 12 and a base housing 14. The base housing 14 has a top edge 16, a bottom wall 18 and a sidewall 20 extending therebetween that form a chamber 22. The sidewalls 20 preferably are angled inwardly from the top edge 16 toward the bottom wall 18 and the base housing 14 is adapted to fit within a conventional cup holder (not shown) of a vehicle. The sidewall 20 has a plurality of air vents 24 that preferably are recessed to permit air flow downwardly between the sidewall 20 and the conventional cup holder and into the air vents 24.

Placed within the chamber 22 of the base housing 14 is a cone filter 26. The cone filter 26 has a first or top ring 28, a bottom wall 30 and a sidewall 32 made of a porous material such as a screen or the like. The diameter of the cone filter 26 is less than the diameter of the base housing 14 to create a space 34 between the sidewall 20 of the base housing 14 and the sidewall 32 of the cone filter 26.

Positioned above and in engagement with the cone filter 26 is a blower 66. Attached to the blower 66 is a main circuit board 70.

Partially disposed within the base housing 14 and positioned above the cone filter 26 is an inner housing 44. The inner housing 44 has an open top 46 with a sidewall 48 and a bottom wall 50 that form a chamber 52. Extending from the bottom wall 50 toward the cone filter 26 is a lip 54. At the open top 46 of the inner housing 44, and extending away from the bottom wall 50 and toward the top housing 12, are a plurality of spaced projections 58. The spaced projections 58 preferably are arcuate having a concave shape in relation to the chamber 52. The bottom wall 50 has a central opening 62. Positioned around the central opening 62, and extending upwardly away from the cone filter are a plurality of alignment prongs 64.

Positioned above the central opening 60 and disposed within the inner housing 44 is a blower 66. The blower 66 has a pair of alignment rings 68 that are cut into opposite corners of the blower 66. The alignment rings 68 are positioned and adapted to receive the alignment prongs 64.

A main circuit board 70 is connected to, positioned above, and engages the blower 66. The main circuit board 70 is held in place by the top housing 12. The top housing 12 has a sidewall 72 and bottom wall 74 that form an open chamber 76. The open chamber 76 is adapted to receive a conventional beverage container (not shown). The sidewall 72 of the top housing 12 is smaller than the diameter of the sidewall 48 of the inner housing 44 to create a conduit 78 between the two sidewalls 48 and 72.

Extending downwardly away from the bottom wall 74 of the top housing 12 toward the bottom wall 50 of the inner housing 44 are alignment tubes 80. The alignment tubes 80 extend past the main circuit board 70 and are positioned and adapted to receive the alignment prongs 64.

A rim 82 extends outwardly and downwardly from a top edge 84 of the top housing 12 in spaced relation to the sidewall 72. Preferably, the rim 82 is arcuate and concave in relation to the sidewall 72 of the top housing 12, with the bottom edge 86. The interior surface 88 is positioned and adapted to connect with a ridge 90 that extends around the top edge 46 of the inner housing 44. The fit between the interior surface 88 and the ridge 90 creates a sealed conduit 92 in the space between the rim 82 and the spaced projections 58. A plurality of recessed portions 94 on the rim offset the spaced projections 58 of the inner housing 44 to form a part of the conduit 92. Aligned with the conduit 92 on the rim 82 are a plurality of air vents 93.

Disposed between the rim 82 and the sidewall 72 of the top housing 12 is a second circuit board 96. The second circuit board 96 is connected to the main circuit board 70, a button or switch 98 and a USB connector 100 in the rim 82. The button 98 extends through an opening in the rim 82 and is received within a button or switch cover 102. The second circuit board 96 is also connected to a glow ring 104. The glow ring 104 is attached to the top edge 84 of the top housing 12.

In operation, power is supplied to the air purifier 10 preferably through a connection between a vehicle 12V utility socket and the USB port 100. The air purifier is activated by engaging the button or switch 98. Upon activation, power is supplied to the glow ring 104 which indicates that the purifier 10 has been activated. A signal is also sent to the main circuit board 70 which in turn activates the blower 66. Upon activation of the blower 66, ambient air is drawn down the side of the purifier and through air vents 24.

From the vents 24 air flows through the filter material 36 and the sidewall 32 of the cone filter 26. The filter material 36 removes airborne particles and gases such as $CO_2$ which are commonly found in vehicles. Once particles and gases are removed, the purified air flows through the filter opening 60 in the top ring 28 of the cone filter 26 and the central opening 62 in the bottom wall 50 of the inner housing 44 in to the conduit 78. From the conduit 78 purified air flows through the conduit 92 and is discharged into the atmosphere through the air vents 93 on the rim 82.

Accordingly, an air purifying device 10 has been disclosed that preserves a vehicle's cup holder function while purifying the air and, at the very least, meets all the stated objectives.

From the above discussion and accompanying figures and claims it will be appreciated that the air purifying device 10 offers many advantages over the prior art. It will be appreciated further by those skilled in the art that other various modifications could be made to the device without parting from the spirit and scope of this invention. All such modifications and changes fall within the scope of the claims and are intended to be covered thereby. It should be understood that the examples and embodiments described herein are for illustrative purposes only and that various modifications or changes in the light thereof will be suggested to persons skilled in the art and are to be included in the spirit and purview of this application.

What is claimed is:

1. A vehicle cup air purifying device, comprising:
   a top housing having a plurality of air vents connected to a base housing having a plurality of air vents;
   a filter disposed within the base housing; and
   a blower disposed within the base housing adapted to draw air through the plurality of air vents in the base housing, through the filter, and discharge the air through the plurality of air vents in the top housing;
   wherein the top housing has a sidewall and a bottom wall that form a chamber adapted to receive a beverage container.

2. The device of claim 1 wherein the plurality of air vents in the base housing are recessed within a sidewall of the base housing.

3. The device of claim 1 wherein the blower is disposed within an inner housing.

4. The device of claim 1 wherein a main circuit board is connected to the blower.

5. The device of claim 1 wherein a rim extends outwardly and downwardly from a top edge of the top housing in spaced relation from the sidewall of the top housing.

6. The device of claim 5 wherein the upper assembly has a bottom edge that is positioned to rest upon the ridge on the top edge of the lower housing.

7. The device of claim 6 wherein the rim has a plurality of recessed portions that offset spaced projections on the inner housing to form conduits that align with the plurality of air vents on the top housing.

8. The device of claim 1 wherein a glow ring is attached to the top housing.

9. The device of claim 1 further comprising a second circuit board connected to a button, a USB port and a main circuit board.

10. The device of claim 1 wherein a side wall of the base housing is angled inwardly from a top edge toward a bottom wall.

11. The device of claim 1 further comprising the filter having a top ring, a bottom wall and a sidewall, wherein the filter has a diameter that is less than the diameter of the base housing thereby forming a space between a sidewall of the base housing and the sidewall of the filter.

12. The device of claim 1 further comprising an inner housing positioned partially disposed within the base housing and positioned above the filter.

13. The device of claim 12 further comprising the inner housing having a central opening with a plurality of alignment prongs positioned around the central opening.

14. The device of claim 13 further comprising the blower having a pair of alignment rings cut into opposite corners of the blower.

15. The device of claim 14 wherein the alignment rings receive a pair of alignment prongs.

16. The device of claim 12 further comprising the inner housing having a bottom wall and a lip extending from the bottom wall toward the filter.

17. The device of claim 1 further comprising a plurality of alignment tubes extends downwardly from the bottom wall of the top housing.

18. The device of claim 4 wherein the main circuit board is held in place by the top housing.

19. A vehicle cup air purifying device, comprising:
    a top housing having a plurality of air vents connected to a base housing having a plurality of air vents;
    a glow ring is attached to the top housing;
    a filter disposed within the base housing; and
    a blower disposed within the base housing adapted to draw air through the plurality of air vents in the base housing, through the filter, and discharge the air through the plurality of air vents in the top housing.

20. A vehicle cup air purifying device, comprising:
    a top housing having a plurality of air vents connected to a base housing having a plurality of air vents;
    a filter disposed within the base housing;
    a blower disposed within the base housing adapted to draw air through the plurality of air vents in the base housing, through the filter, and discharge the air through the plurality of air vents in the top housing; and
    a second circuit board connected to a button, a USB port and a main circuit board.

* * * * *